United States Patent [19]

Zaunbrecher et al.

[11] Patent Number: 5,955,034

[45] Date of Patent: *Sep. 21, 1999

[54] AIR FRESHENER TAPER CANDLE PRODUCT

[75] Inventors: Judith R. Zaunbrecher, Wind Point; Luz P. Requejo, Racine, both of Wis.

[73] Assignee: S. C. Johnson & Son, Inc., Racine, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/915,161

[22] Filed: Aug. 20, 1997

[51] Int. Cl.⁶ .............................. A61L 9/01; A61L 9/02; C10L 5/00; C11C 5/00
[52] U.S. Cl. ............................ 422/126; 44/275; 431/288
[58] Field of Search ................................ 422/5, 126, 305; 44/275; 431/288

[56] References Cited

U.S. PATENT DOCUMENTS

| | | |
|---|---|---|
| 1,974,037 | 9/1934 | Atkins . |
| 2,090,297 | 8/1937 | Knoche . |
| 2,379,250 | 6/1945 | Muskat et al. . |
| 2,415,040 | 1/1947 | Rust . |
| 2,818,615 | 1/1958 | Burness . |
| 2,829,511 | 4/1958 | Oesterle et al. . |
| 3,065,502 | 6/1962 | Lorenian . |
| 3,175,876 | 3/1965 | Fredericks ............................. 422/126 |
| 3,332,428 | 7/1967 | Mold et al. . |
| 3,351,695 | 11/1967 | Hollingsworth . |
| 3,499,452 | 3/1970 | Kallianos et al. . |
| 3,560,122 | 2/1971 | Cassar . |
| 3,577,588 | 5/1971 | Chisholm . |
| 3,630,697 | 12/1971 | Duling . |
| 3,705,890 | 12/1972 | Barker et al. . |
| 3,898,039 | 8/1975 | Lin . |
| 3,940,233 | 2/1976 | Fox et al. . |
| 4,092,988 | 6/1978 | Van Auken et al. . |
| 4,134,714 | 1/1979 | Driskill . |
| 4,155,979 | 5/1979 | Powell . |
| 4,278,658 | 7/1981 | Hooper et al. . |
| 4,302,409 | 11/1981 | Miller et al. . |
| 4,449,987 | 5/1984 | Lindauer . |
| 4,507,077 | 3/1985 | Sapper . |
| 4,568,270 | 2/1986 | Marcus et al. . |
| 4,663,315 | 5/1987 | Hasegawa et al. ................. 422/125 X |
| 4,708,851 | 11/1987 | Freytag Von Loringhoven . |
| 5,068,321 | 11/1991 | Buysch et al. . |
| 5,069,231 | 12/1991 | Rutherford . |
| 5,081,104 | 1/1992 | Orson, Sr. . |
| 5,313,002 | 5/1994 | De Heij et al. . |
| 5,320,798 | 6/1994 | Chambon et al. . |
| 5,538,018 | 7/1996 | Chan et al. . |
| 5,569,779 | 10/1996 | Sabahi et al. . |
| 5,645,845 | 7/1997 | Neumann et al. . |

*Primary Examiner*—Elizabeth McKane

[57] ABSTRACT

This invention provides an air freshener candle product which is a slender combustible body composed of ingredients which comprise (1) candlewax, (2) thermoplastic polymer, (3) particulate polysaccharidic filler, and (4) air freshener ingredient. The air freshener is released into the atmosphere under candle burning conditions. An invention taper-shaped candle is wickless, and can be produced by a continuous molding process.

10 Claims, No Drawings

AIR FRESHENER TAPER CANDLE PRODUCT

BACKGROUND OF THE INVENTION

The subject matter of this patent application is related to that disclosed in patent application POLYMERIC WICK COMPOSITION FOR AIR FRESHENER CANDLE PRODUCT, U.S. Ser. No. 08/915,160, filed Aug. 20, 1997, pending.

BACKGROUND OF THE INVENTION

This invention generally relates to the dispensing of an air freshener from a candle product. More specifically this invention relates to a wickless candle having a content of air freshener ingredient which is released under candle combustion conditions.

Candles have been known and used since early civilization. A typical candle is formed of a solid or semi-solid body of wax such as paraffin wax or beeswax, and it contains an axially embedded combustible fibrous wick.

When the wick of a candle is lit, the generated heat melts the solid wax, and the resulting liquid flows up the wick by capillary action and is combusted.

More recently candles have been developed that appeal to the olfactory as well as the visual sense. This type of candle usually incorporates a fragrance oil in the wax body. As the wax is melted in a lighted candle, there is a release of the fragrance oil from the liquified wax pool.

Conventional fragrance candles have drawbacks because of cost and other considerations. The incorporation of fragrance oil in candlewax is difficult to achieve in a quantity which ensures the release of a suitable level of fragrance into the atmosphere during candle burning. Further, the incorporated fragrance tends to migrate and volatilize from the wax body prematurely. The fragrance also softens the wax body, and there is an undesirable loss of rigidity in the candle structure.

There is continuing interest in the development of improved fragrance and other types of air freshener candle products.

Accordingly, it is an object of this invention to provide an air freshener candle product which releases air freshener into the atmosphere only under the combustion conditions of the burning candle.

It is another object of this invention to provide a taper-shaped wickless air freshener candle product.

It is a further object of this invention to provide an air freshener candle product which can be produced by a continuous molding process.

Other objects and advantages of the present invention shall become apparent from the accompanying description and examples.

Publications of background interest relative to the present invention include U.S. Pat. Nos. 2,829,511; 2,818,615; 3,560,122; 3,630,697; and 3,940,233; incorporated by reference.

U.S. Pat. No. 2,829,511 describes a candle wick structure composed of a core strand of cellulose acetate in combination with an outer web of cotton fibers.

U.S. Pat. No. 3,560,122 describes a wick composition which is composed of paraffin wax, polyethylene and particulate palygorskite clay.

DESCRIPTION OF THE INVENTION

One or more objects of the present invention are accomplished by the provision of an air freshener candle product which is a taper-shaped combustible body comprising:

(a) between about 25–85 weight percent of candlewax ingredient;
(b) between about 10–45 weight percent of thermoplastic polymer ingredient; and
(c) between about 0.5–30 weight percent of particulate polysaccharidic filler ingredient; and
(d) between about 0.05–15 weight percent of air freshener ingredient;

wherein the air freshener ingredient is released into the atmosphere under candle burning conditions.

The term "taper-shaped" as employed herein refers to a slender candle body which can be rigid, semi-rigid or flexible, and which can be circular, square, rectangular oval, hexagonal, or any other geometric shape for esthetic appeal. A typical cylindrical candle body can have a diameter between about 0.3–1.5 centimeters.

The candlewax ingredient can be selected from commercially available wax media. The combustible body of a candle product typically is a thermoplastic blend of organic materials such as beeswax, paraffin wax, montan wax, carnauba wax, microcrystalline wax, fatty alcohols, fatty acids, fatty esters, and the like.

The polymer ingredient of an invention air freshener candle product preferably is selected from the class of thermoplastic resins which in general are adapted for fiber-formation by processes such as extrusion or compression molding. It is preferred that the polymer is composed of elements which do not convert into noxious vapors under candle combustion conditions, such as carbon, hydrogen and oxygen.

Equipment and processes for polymer fiber-formation by extrusion are described in publications such as U.S. Pat. Nos. 3,065,502; 3,351,695; 3,577,588; 4,134,714; 4,302,409; and 5,320,798; incorporated by reference.

Suitable fiber-forming polymers include hydrocarbyl polyolefinic derivatives such as low and high density polyethylene, low and high density polypropylene, polybutene, polystyrene, and the like.

Other types of suitable polymers include polyvinyl acetate, and acrylate resins such as polymethyl acrylate, polymethyl methacrylate, polybutyl methacrylate, poly (ethyl acrylate/ethylene), and the like.

Other types of polymers such as thermoset resins can be utilized by pressure molding a powder blend of candlewax, resin, cellulosic filler and fragrance ingredients. Other components can be included in a candle composition such as stearic acid, polyoxyalkylene glycol, and the like.

The polysaccharidic filler ingredient of an invention candle product typically is in the form of a powder, or in the form of fine fibers which have an average length between about 0.3–3 centimeters.

The term "polysaccharidic" as employed herein is meant to include natural products such as sugars, starches, hydrocolloid gums, cellulosics, and the like.

A cellulosic filler ingredient can be obtained from vegetable sources such as cotton, linen, flax, hemp, jute, wood pulp, and the like. A cellulosic filler can be in the form of substituted derivatives such as cellulose acetate or methylcellulose.

The term "cellulosic" as employed herein refers to a β-glucosidic polysaccharide corresponding to the formula:

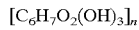

where n is an integer which provides an average molecular weight between about 100,000–2,000,000.

Formation of an invention air freshener candle product can be accomplished by the extrusion of a molten or particulate blend of the candle ingredients, or by compression molding of the blended ingredients.

The term "air-freshener" as employed herein is meant to include fragrances such as geraniol, insect repellants such as citronellal, and therapeutic agents such as menthol.

An air freshener ingredient of a present invention candle product can be any inherently volatile organic compound which is capable of being dispersed into the atmosphere when the candle product is burning.

Suitable volatile air freshener compounds include limonene, α-terpinene, α-pinene, camphene, undecanol, 4-isopropylcyclohexanol, geraniol, linalool, citronellol, farnesol, menthol, 3-trans-isocamphylcyclohexanol, benzyl alcohol, 2-phenylethyl alcohol, 3-phenylpropanol, 3-methyl-5-phenylpentanol, cinnamic alcohol, isoborneol, thymol, eugenol, isoeugenol, anise alcohol, methyl salicylate, and the like.

Other suitable air freshener compounds include aldehydes and ketones such as hexanal, decanal, 2-methyldecanal, trans-2-hexenal, acetoin, diacetyl, geranial, citronellal, methoxydihydro-citronellal, menthone, carvone, camphor, fenchone, ionone, irone, damascone, cedryl methyl ketone, muscone, civetone, 2,4-dimethyl-3-cyclohexene carboxaldehyde, 2-heptylcyclopentanone, cis-jasmone, dihydrojasmone, cyclopentadecanone, benzaldehyde, phenylacetaldehyde, dihydrocinnamaldehyde, cinnamaldehyde, α-amylcinnamaldehyde, acetophenone, benzylacetone, benzophenone, piperonal, and the like.

Other suitable air freshener compounds include esters such as trans-2-hexenyl acetate, allyl 3-cyclohexylpropionate, methyl cinnamate, benzyl cinnamate, phenylethyl cinnamate, and the like.

Other suitable air freshener compounds include crystalline fragrance materials with a high vapor pressure, such as vanillin, ethyl vanillin, coumarin, tonalid, calone, heliotropene, musk xylol, cedrol, musk ketone, benzophenone, raspberry ketone, methyl naphthyl ketone beta, phenyl ethyl salicylate, veltol, maltol, maple lactone, proeugenol acetate, evernyl, and the like.

The present invention also contemplates a candle product in which the air freshener is a constituent of a nonvolatile air freshener-release additive.

The term "nonvolative" as employed herein refers to an organic compound which has a low vapor pressure under ambient conditions.

The chemical-bonding of a volatile alcohol air freshener such as geraniol or menthol to another organic compound to form a nonvolatile organic derivative can be accomplished by the formation of a carbonate ester linkage (as illustrated in Example V):

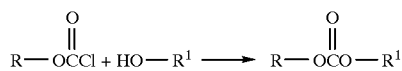

The chemical-bonding of an aldehyde such as citronellal or a ketone such as fenchone to another organic compound can be accomplished by the formation of a hemiacetal (ketal) and/or acetal (ketal) linkage under acidic conditions:

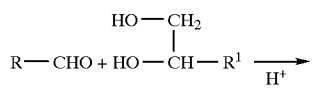

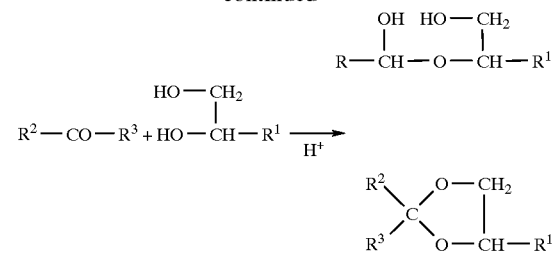

The chemical bonding of an ester such as phenylethyl cinnamate air freshener to another organic compound can be accomplished by a Michael addition reaction under alkaline conditions:

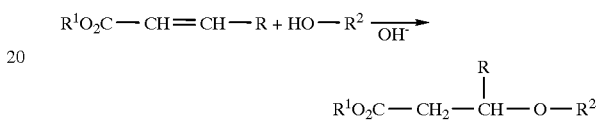

The Michael addition reaction is described in publications such as U.S. Pat. No. 2,415,040 and U.S. Pat. No. 5,569,779; incorporated by reference.

Another chemical means for forming a linkage between a volatile alcohol air freshener and another organic compound is by the use of an alcohol epichlorohydrin derivative under alkaline reaction conditions:

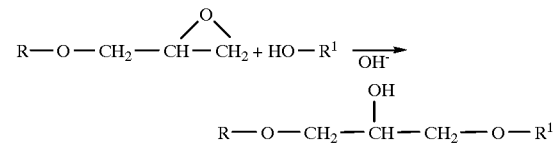

A present invention air freshener candle product provides significant advantages not previously contemplated in the candle making art. An invention candle product is wickless, and can be produced economically by a continuous extrusion process. A preferred invention candle product also burns with a clean bright flame, and there is little or no wax dripping or residual ash formation.

A present invention air freshener candle product also can be extruded into a flexible taper filament which can be spiral wound for incorporation in an air freshener dispensing device.

The following examples are further illustrative of the present invention. The components and specific ingredients are presented as being typical, and various modifications can be derived in view of the foregoing disclosure within the scope of the invention.

EXAMPLE I

This Example illustrates the preparation of an air freshener candle product in accordance with the present invention.

Cellulose powder is impregnated with geraniol, and the admixture is blended with polyethylene powder (MP 120° C.) and paraffin wax flakes (MP 55° C.). The blend is passed through an extruder under heat and pressure to form a rigid circular-shaped candle matrix (6 millimeters diameter).

The candle product consists of paraffin wax (60 weight percent), polyethylene (25 weight percent), cellulose powder (14 weight percent), and geraniol (1.0 weight percent).

A cut section of the continuous extrusion candle product is ignited, and a flame persists until the candle is completely consumed. The combustion releases a flowery rose aroma which is characteristic of geraniol.

Similar results are obtained where starch or guar gum is substituted for the cellulose powder.

EXAMPLE II

This Example illustrates the preparation of an air freshener candle product in accordance with the present invention.

Polypropylene powder (MP 110° C.), and beeswax (MP 66° C.) and blended with an admixture of cellulose powder and ethylvanillin. The blend is passed through an extruder under heat and pressure to form a rigid square-shaped candle matrix (3×3 millimeters).

The candle product consists of beeswax (68 weight percent), polypropylene (12 weight percent), cellulose powder (18 weight percent), and ethylvanillin (2.0 weight percent).

A cut section of the continuous extrusion candle product is ignited, and a flame persists until the candle is completely consumed. A sweet vanillin-like aroma is detectable in the atmosphere during the candle combustion.

Similar results are obtained when the polymer ingredient is polyvinyl acetate.

EXAMPLE III

This Example illustrates the preparation of nonvolatile air freshener-release saccharide derivatives of ketone and aldehyde air freshener constituents.

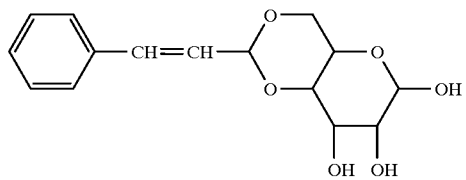

Glucose (180 g) is dissolved in dimethylformamide (4 liters), and Amberlite 1R-120 (100 g) is added. The mixture is heated to 80EC, and cinnamaldehyde dimethyl acetal (178 g) is added in portions over a three hour period. After the addition, the mixture is heated for an additional hour.

The ion exchange resin is removed by filtration, and the solvent and excess cinnamaldehyde dimethyl acetal are removed by vacuum distillation. The residual material is recrystallized from 95% ethanol to give 150 g of 4,6-O-cinnamylidene-D-glucopyranose product.

Following the same procedure, the D-glucopyranose acetal and ketal derivatives of the following aldehydes and ketones are synthesized:

| | |
|---|---|
| decanal | menthone |
| geranial | fenchone |
| citronellal | acetophenone |
| benzaldehyde | benzophenone |
| phenylacetaldehyde | camphor |
| dihydrocinnamaldehyde | geranylacetone |

A blend is prepared with paraffin wax 10% microcrystalline wax (MP 68E-71EC), polyethylene powder (MP 120EC), cellulose fibers (0.5 cm average length), and 4,6-O-cinnamaldehyde-D-glucopyranose air freshener-release additive. The blend is passed through an extruder under heat and pressure to form a rigid oval-shaped candle matrix (12×8 millimeters cross-section).

The candle product consists of candlewax (30 weight percent), polyethylene (43 weight percent), cellulose fibers (24.5 weight percent), and air freshener-release additive (2.5 weight percent).

A cut section of the continuous extrusion candle product is completely consumed when ignited. A cinnamaldehyde scent is perceptible in the atmosphere during the candle combustion.

Similar olfactory results are obtained with each of the other synthesized aldehyde and ketone air freshener-release derivatives as additives in present invention candle products.

EXAMPLE IV

This Example illustrates the preparation of menthyl chloroformate.

A reactor in a dry-ice/acetone bath (−75° C.) is charged with liquid phosgene (117 g). Menthol (130 g), dissolved in 500 mL of cyclopentane, is added dropwise to the phosgene with stirring. The reaction medium is refluxed for six hours at room temperature. The excess phosgene and cyclopentane are removed under reduced pressure.

The recovered menthyl chloroformate is dissolved in diethyl ether (300 mL), and the solution is washed with aqueous sodium bicarbonate, and then with distilled water. The liquid medium is dried over sodium sulfate, and the solvent is removed under reduced pressure to yield a purified menthyl chloroformate.

EXAMPLE V

This Example illustrates the preparation of a nonvolatile air freshener-release dicarbonate ester of alcohol air freshener constituents.

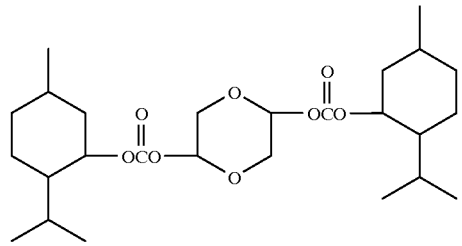

To a cooled solution of pyridine (25 mL) in chloroform (500 mL) is added with stirring glycolaldehyde (10 g, 0.167 mole). A solution of menthyl chloroformate (36.5 g; 0.167 mole) in chloroform (100 mL) is added dropwise. Stirring is continued for 30 minutes at 0° C., then for 18 hours at room temperature. The reaction medium is washed with aqueous sodium bicarbonate, and then dried over sodium sulfate.

The solvent is removed under reduced pressure. The residual product is recrystallized from chloroform:hexane to yield 16 g of 2,5-bis(menthylcarbonyloxy)-1,4-dioxane.

Following the same procedure, the dicarbonate ester derivatives of the following alcohols are synthesized:

| | |
|---|---|
| geraniol | eugenol |
| linalool | 3-phenylpropanol |
| citronellol | cinnamyl alcohol |
| benzyl alcohol | terpineol |

A blend is prepared with montan wax (MP 81°–85° C.), polystyrene powder (MP 115° C.), cellulose powder, and 2,5-bis(menthylcarbonyloxy)-1,4-dioxane air freshener-release additive. The blend is passed through an extruder under heat and pressure to form a semi-rigid circular-shaped candle matrix (4 millimeters diameter).

The candle product consists of montan wax (65 weight percent), polystyrene (17 weight percent), cellulose powder (12 weight percent), and air freshener-release additive (6.0 weight percent).

A cut section of the continuous extrusion product is completely consumed when ignited. A distinct aroma of menthol is detectable in the atmosphere during the candle burning.

Similar olfactory results are obtained with each of the other synthesized aldehyde and ketone air freshener-release derivatives as additives in the present invention candle products.

What is claimed is:

1. A wickless taper shaped combustible air freshener candle comprising:
   (a) between about 25–85 weight percent of candlewax;
   (b) between about 10–45 weight percent of thermoplastic polymer;
   (c) between about 0.5–15 weight percent of particulate polysaccharidic filler; and
   (d) between about 0.05–15 weight percent of a non-volatile air freshener formed by chemically bonding a volatile air freshener compound to an organic compound that is different from the air freshener;

wherein said candle is produced by a continuous molding process, and said air freshener is dispersed into the atmosphere under candle burning conditions.

2. A candle as set forth in claim 1 which is cylindrical in shape and has a diameter of from about 03. to about 1.5 centimeters.

3. A candle as set forth in claim 2 wherein said polymer comprises a polyolefinic resin.

4. A candle as set forth in claim 2 wherein said polymer is selected from the group consisting of polyethylene, polypropylene, polystyrene, and polyvinyl acetate polymers.

5. A candle as set forth in claim 2 wherein said particulate polysaccharidic filler is selected from the group consisting of sugars, starches, hydrocolloid gums, and cellulosics.

6. A candle as set forth in claim 5 wherein said particulate polysaccharidic filler is selected from the group consisting of cellulose and cellulose derivatives.

7. A candle as set forth in claim 1 wherein said air freshener comprises a fragrance ingredient.

8. A candle as set forth in claim 1 wherein said air freshener comprises an insect repellant ingredient.

9. A candle as set forth in claim 1 wherein said air freshener comprises a therapeutic ingredient.

10. A candle as set forth in claim 1 wherein said air freshener comprises an ingredient selected from the group consisting of geraniol, citranellal, and menthol.

* * * * *

UNITED STATES PATENT AND TRADEMARK OFFICE
CERTIFICATE OF CORRECTION

PATENT : 5,955,034

DATED : September 21, 1999

INVENTOR(S) : Judith R. Zaunbrecher et al

It is certified that error appears in the above-identified patent and that said Letters Patent is hereby corrected as shown below:

Column 8, line 9, "about 03." should read --about 0.3--.

Signed and Sealed this

First Day of August, 2000

Attest:

Attesting Officer

Q. TODD DICKINSON

Director of Patents and Trademarks